United States Patent
Okubo et al.

(10) Patent No.: US 11,654,215 B2
(45) Date of Patent: May 23, 2023

(54) EMBOLIZATION COIL AND METHOD FOR PRODUCING EMBOLIZATION COIL

(71) Applicant: TANAKA KIKINZOKU KOGYO K.K., Tokyo (JP)

(72) Inventors: Michimasa Okubo, Hiratsuka (JP); Kenji Goto, Hiratsuka (JP)

(73) Assignee: TANAKA KIKINZOKU KOGYO K.K., Tokyo (JP)

(*) Notice: Subject to any disclaimer, the term of this patent is extended or adjusted under 35 U.S.C. 154(b) by 226 days.

(21) Appl. No.: 16/069,955

(22) PCT Filed: Mar. 2, 2017

(86) PCT No.: PCT/JP2017/008231
§ 371 (c)(1),
(2) Date: Jul. 13, 2018

(87) PCT Pub. No.: WO2017/154717
PCT Pub. Date: Sep. 14, 2017

(65) Prior Publication Data
US 2019/0030215 A1 Jan. 31, 2019

(30) Foreign Application Priority Data

Mar. 7, 2016 (JP) .............................. JP2016-043010

(51) Int. Cl.
*A61L 31/02* (2006.01)
*C22C 5/02* (2006.01)
(Continued)

(52) U.S. Cl.
CPC ............ *A61L 31/022* (2013.01); *A61B 17/12* (2013.01); *A61B 17/1214* (2013.01);
(Continued)

(58) Field of Classification Search
CPC .......... C22C 5/02; C22C 5/04; A61B 17/1214; B21F 3/00; A61L 2430/36; C22F 1/006; C22F 1/14
See application file for complete search history.

(56) References Cited

U.S. PATENT DOCUMENTS 4,994,069 A * 2/1991 Ritchart ........... A61B 17/12022
606/191
5,472,333 A * 12/1995 van der Zel .......... C03B 37/095
148/405
(Continued)

FOREIGN PATENT DOCUMENTS

EP 3015559 A1 5/2016
EP 3085797 A1 10/2016
(Continued)

OTHER PUBLICATIONS

JP5582484B1: Espacenet English machine translation (Year: 2014).*
(Continued)

*Primary Examiner* — Keith Walker
*Assistant Examiner* — Adil A. Siddiqui
(74) *Attorney, Agent, or Firm* — Orrick, Herrington & Sutcliffe LLP; Joseph A. Calvaruso; K. Patrick Herman

(57) ABSTRACT

The present invention is an embolization coil having an optimum morphological stability. The embolization coil includes a wire material made of an Au—Pt alloy. The wire material constituting the embolization coil has such a composition that a Pt concentration is 24 mass % or more and less than 34 mass %, with the balance being Au. The wire material has such a material structure that a Pt-rich phase of an Au—Pt alloy having a Pt concentration of 1.2 to 3.8 times a Pt concentration of an α phase is distributed in an α phase matrix. The wire material has a bulk susceptibility of −13 ppm or more and −5 ppm or less. In a material structure of a transverse cross-section of the wire material, an average (Continued)

value of two or more average crystal particle diameters measured by a linear intercept method is 0.20 μm or more and 0.35 μm or less.

5 Claims, 5 Drawing Sheets

(51) Int. Cl.
    *C22F 1/14* (2006.01)
    *A61B 17/12* (2006.01)
    *B21F 3/00* (2006.01)
    *C22C 1/02* (2006.01)
    *C22F 1/00* (2006.01)
    *A61B 17/00* (2006.01)

(52) U.S. Cl.
    CPC ............... *A61L 31/02* (2013.01); *B21F 3/00* (2013.01); *C22C 1/02* (2013.01); *C22C 5/02* (2013.01); *C22F 1/14* (2013.01); *A61B 2017/00526* (2013.01); *A61B 2017/00836* (2013.01); *A61B 2017/00964* (2013.01); *C22F 1/00* (2013.01)

(56) References Cited

U.S. PATENT DOCUMENTS

| | | | |
|---|---|---|---|
| 2005/0267494 A1* | 12/2005 | Iwata | A61L 31/10 606/151 |
| 2009/0191089 A1* | 7/2009 | Agarwal | C22C 5/02 420/511 |
| 2012/0035632 A1 | 2/2012 | Hamada et al. | |
| 2017/0029927 A1* | 2/2017 | Shima | C22C 5/02 |
| 2017/0245865 A1* | 8/2017 | Jones | A61B 17/12145 |

FOREIGN PATENT DOCUMENTS

| | | | | |
|---|---|---|---|---|
| JP | 2013-106829 A | 6/2013 | | |
| JP | 5582484 B1 * | 9/2014 | | C22F 1/14 |
| JP | 5582484 B1 | 9/2014 | | |
| JP | 2015-7277 A | 1/2015 | | |
| WO | WO 2010/084948 A1 | 7/2010 | | |

OTHER PUBLICATIONS

Extended Search Report for EP Appl. No. 17763057.1, dated Dec. 19, 2018.
International Search Report for PCT/JP2017/008231, dated May 23, 2017.

* cited by examiner

FIG. 2

| Treatment temperature | 300°C | 500°C | 700°C |
|---|---|---|---|
| Observed image | | | |
| Draw lines ↑ Count intersections | | | |

EMBOLIZATION COIL AND METHOD FOR PRODUCING EMBOLIZATION COIL

TECHNICAL FIELD

The present invention relates to an embolization coil, which is a kind of medical instrument. The present invention also relates to a method for producing the embolization coil. More specifically, the present invention relates to an embolization coil that has an excellent morphological stability and that makes an artifact less likely to occur in a magnetic environment such as in a magnetic resonance imager.

RELATED ART

In treatment of cerebrovascular accidents such as subarachnoid hemorrhage, coil embolization has attracted attention recently as treatment for preventing rapture of cerebral aneurysm. This medical treatment is a method that includes: inserting a catheter into an artery such as femoral artery; guiding the catheter to cervical artery; further from the cervical artery, inserting a micro-catheter into the cerebral aneurysm; and stuffing the cerebral aneurysm with a coil and the retaining the coil in the cerebral aneurysm. Coils are repeatedly stuffed and retained in the aneurysm until the aneurysm is completely filled with coils. In this respect, embolization coils used in coil embolization are fine metal wires wound into a coil shape. In particular, embolization coils having a secondary coil shape are well-known.

Embolization coils are medical instruments implanted in human bodies, and as such, are required to have biocompatibility and excel in anti-corrosion property. In light of the circumstances, metal materials such as Pt, Pt—W alloy, stainless, and Ti alloy have been conventionally employed as constituent materials of embolization coils.

Incidentally, magnetic resonance imagers (MRI) are used on recent medical front lines in a wide variety of examinations and surgeries. In magnetic environments of MRI, there is a concern over artifacts (false images) caused by embolization coils. An artifact refers to such a phenomenon that an MRI image is distorted by a difference between the magnetic susceptibility of a metal in a magnetic field and the magnetic susceptibility of a biological tissue in a region around the magnetic field. An artifact can hinder accurate diagnoses and accurate surgeries, and it is therefore necessary to minimize artifact occurrences.

A material property to consider in investigating artifact problems in magnetic field environments is magnetic susceptibility (bulk susceptibility). This is based on the assumption that by decreasing the difference between the magnetic susceptibility of a constituent material of an embolization coil and the magnetic susceptibility of a biological tissue in which the embolization coil is implanted, artifact occurrences can be minimized. Specifically, a material deemed suitable is small in difference of magnetic susceptibility relative to the magnetic susceptibility ($-9$ ppm ($-9\times10^{-6}$)) of water, which is a main constituent of a biological tissue. In this respect, the above-described metal materials with a history of practice have had such a problem that there is a large difference in magnetic susceptibility relative to biological tissues.

In light of the circumstances, it is necessary to develop a material with artifact-free take into considerations. In light of this necessity, the Applicant of the present application presented an Au—Pt alloy as an artifact-free metal material (patent document 1). The Au—Pt alloy has a predetermined metal structure and is made of Pt of 24 mass % or more and less than 34 mass %, with the balance being Au. This Au—Pt alloy is a metal material obtained by: alloying Au, which is a diamagnetic metal (magnetic susceptibility: $-34$ ppm), and Pt (magnetic susceptibility: $+279$ ppm); and distributing predetermined metal phases ($\alpha$ phase and Pt-rich phase) in the alloy in a desired manner, thereby making the magnetic susceptibility of the alloy as a whole approximate to the magnetic susceptibility of water.

Specifically, the magnetic susceptibility of the alloy is adjusted by, as well as by adjusting the alloy composition by employing the above-described ranges, adjusting the material structure of the alloy by forming a mixed phase structure in which a Pt-rich phase higher in Pt concentration than the $\alpha$ phase is deposited in the $\alpha$ phase matrix. The $\alpha$ phase is an Au—Pt alloy phase predicted from the phase diagram of Au—Pt system alloy illustrated in FIG. 1. The Pt-rich phase is an Au—Pt alloy phase having a Pt concentration of 1.2 times to 3.8 times the Pt concentration of the $\alpha$ phase. Since the Pt-rich phase is higher in Pt concentration, the magnetic susceptibility of the Pt-rich phase is shifted further toward the positive side than the magnetic susceptibility of the $\alpha$ phase. In the Au—Pt alloy recited in patent document 1, the distribution amount of the Pt-rich phase is adjusted so that the magnetic susceptibility of the alloy as a whole is $-13$ ppm or more and $-5$ ppm or less. The distribution amount of the Pt-rich phase is adjusted such that the Pt-rich phase has an area ratio of 1 to 22% on an arbitrary cross-section of the alloy.

The Applicant of the present application confirmed that this Au—Pt alloy exhibited a magnetic susceptibility ($-13$ ppm or more and $-5$ ppm or less) of $\pm 4$ ppm relative to the magnetic susceptibility of water. The Applicant also confirmed that this Au—Pt alloy was artifact-free as a result of an image pick-up test using an actual MRI. Thus, this Au—Pt alloy has been confirmed as a promising medical-use material. Also, the constituent elements Au and Pt of the Au—Pt alloy both have biocompatibility and excel in anti-corrosion property, thus meeting essential characteristic requirements.

RELATED ART DOCUMENTS

Patent Documents

[Patent document 1] JP 5582484B.

SUMMARY

Problems to be Solved by the Invention

Requirements of embolization coils have been described so far in terms of characteristics of constituent materials. There are also requirements from functional points of view as medical instruments. Specifically, an embolization coil is an appliance that passes through blood vessels and stuffs an aneurysm with the embolization coil, thereby occluding the aneurysm. This requires that the embolization coil, even though deformed during delivery through the human body, be able to restore a predetermined shape upon reaching the aneurysm.

As described above, a typical embolization coil has a secondary coil shape. A secondary coil shape is formed by subjecting a fine wire material to winding processing (primary coil processing) at a minute curvature and subjecting the obtained spiral wire material to additional winding processing (secondary coil processing). In this respect, the primary coil processing is performed at a processing rate high enough that the resulting wire material is a spiral without a processing return. In contrast, the secondary coil processing is performed at a processing rate lower than the processing rate of the primary coil processing and may meet with a processing return after processing. Also, the coil may have a secondary coil shape immediately after the secondary coil processing, but may lose shape at the time when the coil is used as an embolization coil.

Thus, embolization coils are required to be morphologically stable enough to maintain a shape that has been set and, even though the shape may be deformed by load involved while embolization coils are used, easily restore the shape upon removal of the load. In this respect, the above-described artifact-free metal material made of the Au—Pt alloy presented by the Applicant of the present application has a processability optimum enough to be coil-processable without material breakage.

However, due consideration has not been given to the Au—Pt alloy presented by the Applicant of the present application as to morphological stability of the Au—Pt alloy in the case where the Au—Pt alloy is processed into an embolization coil, which is a specific application. In light of the circumstances, the present invention provides an embolization coil to which a wire material made of the Au—Pt alloy is applied and which has an optimum morphological stability. The present invention also provides a method for producing the embolization coil. This object is under the assumption that for the purpose of implementing an artifact-free configuration, the magnetic susceptibility of a metal material remains unchanged.

Means of Solving the Problems

The inventors examined a production process of an embolization coil under the assumption that the Au—Pt alloy (patent document 1) presented by the Applicant of the present application is applied to the embolization coil. The embolization coil is produced by processing a fine wire material (having a wire diameter of 100 μm or less). This wire material is produced by processing an Au—Pt alloy material (an ingot or a material obtained by roughly processing an ingot) at a high processing rate. This production process also applies in the Au—Pt alloy presented by the Applicant of the present application. It should be noted, however, that the Au—Pt alloy cannot undergo treatment that involves high-temperature heat in the process between production of the alloy material and processing of the alloy material into an embolization coil. As described above, the magnetic susceptibility of the Au—Pt alloy is adjusted by implementing a mixed phase structure of α phase and Pt-rich phase. Heat treatment may cause changes in phase configuration and, therefore, should be avoided.

Concurrently with the above examination, the inventors made an assumption that some thermomechanical treatment is necessary for imparting morphological stability to an Au—Pt alloy processed into a wire material. In light of the circumstances, the inventors conducted extensive study and found that by subjecting an Au—Pt alloy wire material to coil processing while subjecting the Au—Pt alloy wire material to predetermined thermomechanical treatment, an optimum morphological stability is imparted to the resulting coil. The inventors conducted study on the Au—Pt alloy wire material of the coil produced using the thermomechanical treatment, detailed later. As a result, the inventors found that the Au—Pt alloy wire material can be characterized in terms of material structure.

Specifically, the present invention is an embolization coil including a wire material made of an Au—Pt alloy. The wire material constituting the embolization coil has such a composition that a Pt concentration is 24 mass % or more and less than 34 mass %, with the balance being Au. The wire material has such a material structure that a Pt-rich phase of an Au—Pt alloy having a Pt concentration of 1.2 to 3.8 times a Pt concentration of an α phase is distributed in an α phase matrix. The wire material has a bulk susceptibility of −13 ppm or more and −5 ppm or less. In a material structure of a transverse cross-section of the wire material, an average value of two or more average crystal particle diameters measured by a linear intercept method is 0.20 μm or more and 0.35 μm or less.

A configuration of the embolization coil according to the present invention will be described in detail below. As described above, the present invention is an embolization coil made of a predetermined Au—Pt alloy wire material. In light of this, an Au—Pt alloy and an Au—Pt alloy wire material constituting an embolization coil will be described first. As has been described hereinbefore, the Au—Pt alloy applied to the present invention is equivalent in composition and phase configuration to the Au—Pt alloy presented by the Applicant of the present application and recited in patent document 1. Application of an Au—Pt alloy is because if Pt is solid-dissolved in Au, which is a diamagnetic metal, an alloy phase with adjusted magnetic susceptibility appears. As seen from the Au—Pt system phase diagram illustrated in FIG. 1, Pt and Au are easily alloyable, and the composition range including the region of the α phase, which is an all proportional solid solution, spreads over a comparatively wide area. The Au—Pt alloy applied to the present invention has such an alloy composition that the Pt concentration is 24 mass % or more and less than 34 mass %. This composition range ensures that α phase with stable magnetization properties is deposited.

The Au—Pt alloy applied to the present invention has such a mixed phase material structure that with α phase forming a matrix, Pt-rich phase is distributed in the matrix. That is, with Pt-rich phase deposited in α phase, the magnetic susceptibility of the alloy as a whole is adjusted utilizing the difference in magnetic susceptibility between the two phases. The Pt-rich phase is an Au—Pt alloy phase having a Pt concentration of 1.2 times to 3.8 times the Pt concentration of the α phase. The distribution amount of the Pt-rich phase is adjusted so that the magnetic susceptibility of the alloy as a whole is −13 ppm or more and −5 ppm or less.

The embolization coil according to the present invention has, in terms of composition, a basic configuration of an Au—Pt alloy made of the above-described constituent materials. With this basic configuration, the embolization coil has features in the material structure that the Au—Pt alloy wire material has after formed into an embolization coil. One of the features of the present invention in terms of material structure is average crystal particle diameter. An average crystal particle diameter refers to an average value of particle diameters of crystals surrounded by a manifest grain boundary in an observation region arbitrarily set on the material. That is, the average crystal particle diameter used herein is calculated without regard to the kind of crystal (α phase or Pt-rich phase). In the present invention, a plurality of average crystal particle diameters values are measured, and an average value of the average crystal particle diameter values is obtained. A requisite is that the average value is 0.20 μm or more and 0.35 μm or less.

As described above, an average crystal particle diameter refers to a general particle size with no particular crystal (phase) in focus. This feature that the wire material constituting the embolization coil according to the present invention has in terms of material structure consists of a process of producing the wire material from an alloy material and a process of winding the wire material into a coil shape.

As described earlier, in the process of producing the wire material from an Au—Pt alloy material, the material should not be heated at high temperature. The Au—Pt alloy according to the present invention has an optimum magnetic susceptibility, which is implemented by causing a mixed phase structure of α phase and Pt-rich phase to appear. Avoidance of high-temperature heating is because it may cause the mixed phase structure to collapse. In light of this, the processing to obtain the Au—Pt alloy wire material is implemented by processing that causes no structural changes, such as processing at comparatively low temperatures and cold working. Also, the processing of the material into a fine wire material for the embolization coil is performed at a high processing rate. This makes the crystal particles of the mixed phase structure of α phase and Pt-rich phase finer in the process of producing the wire material while maintaining the mixed phase structure.

The produced wire material is subjected to winding processing into a coil shape, resulting in an embolization coil. In the present invention, morphological stability treatment, which is for imparting morphological stability, is performed in the process of obtaining a coil shape. Morphological stability treatment is a kind of heat treatment that heats a wire material secured in a coil shape state, which will be detailed later. Since morphological stability treatment is heat treatment, the mixed phase structure of fine α phase and fine Pt-rich phase may be subject to change. The inventors examined the material structure of the Au—Pt alloy wire material of an embolization coil that excelled in morphological stability and magnetic susceptibility as a result of optimum morphological stability treatment. As a result, the inventors found that the crystal particle diameter (average crystal particle diameter) in the material structure was within a predetermined range.

Specifically, in the present invention, in the material structure of a transverse cross-section of the Au—Pt alloy wire material, the average crystal particle diameter is specified at 0.20 μm or more and 0.35 μm or less. If the average crystal particle diameter is less than 0.20 μm, the morphological stability is insufficient, making substantially no difference from the morphological stability of the wire material before it is processed into a coil shape. If the average crystal particle diameter is in excess of 0.35 μm, the magnetic susceptibility of the Au—Pt alloy wire material is outside the preferable range, resulting in an embolization coil that cannot be regarded as artifact-free. From the viewpoint of magnetic susceptibility, the average crystal particle diameter is preferably 0.25 μm or more and 0.33 μm or less.

In the present invention, a value measured by a linear intercept method is employed as the average crystal particle diameter. The linear intercept method is a method that, while being comparatively easy for measuring average crystal particle diameter, ensures accurate values if the method is performed properly. The linear intercept method as a measurement method may be performed in any manner known in the art; a specific example will be described later by referring to the embodiment described later.

In the present invention, the average crystal particle diameter is measured a plurality of times by the linear intercept method in one field of vision of a structure observed image of the transverse cross-section. The average crystal particle diameter is specified by the average value of the plurality of average crystal particle diameters values. The average crystal particle diameter is measured preferably 20 times or more, and more preferably, 30 times or more. Then, the average value of the measured values is calculated. While the number of times of measurement is preferably as many as possible, the upper limit is preferably 50 times or less, from the viewpoint of a balance between efficiency and measurement accuracy.

Thus, when the Au—Pt alloy wire material is subjected to morphological stability treatment, a first change to occur in the mixed phase structure is a change in the crystal particle diameter (average crystal particle diameter). In this respect, according to study conducted by the inventors, another possible structural change to occur, other than a change in the crystal particle diameter, is generation and growth of a separate phase. A separate phase refers to α phase generated from part of the phase (α phase and/or Pt-rich phase) that has existed since before the separate phase was generated. The inventors assume that the separate phase is an alloy phase similar to the Pt-rich phase, which has a higher Pt concentration than the α phase. Although the composition of the separate phase need not be clearly understood, the separate phase should be prevented from occurring in order to keep the magnetic susceptibility within a proper range.

A convenient way of checking whether the separate phase has been deposited is to examine a variation of a plurality of average crystal particle diameters that have been measured. The particle diameter of the separate phase at its initial stage is smaller than the particle diameter of the surrounding phase. This leads to the prediction that the average crystal particle diameter varies depending on the amount of the separate phase. In light of this, in the embolization coil according to the present invention, a standard deviation of a plurality of average crystal particle diameter values that have been measured is preferably 0.025 or more and 0.085 or less. This is regarded as state in which there is less of the separate phase in the Au—Pt alloy wire material. A more preferable range of the standard deviation is 0.030 or more and 0.082 or less.

When an Au—Pt alloy wire material has a standard deviation in excess of 0.085, an excessive amount of separate phase is generated in the Au—Pt alloy wire material. This Au—Pt alloy wire material does not result in an artifact-free embolization coil, whose magnetic susceptibility is within a proper range. While the standard deviation is preferably as small as possible, study conducted by the inventors shows that an embolization coil having a standard deviation of less than 0.025 is likely to be inferior in morphological stability.

In the embolization coil according to the present invention, the Au—Pt alloy wire material preferably has a tensile strength of 800 MPa or more, and more preferably, 1000 MPa or more. While the tensile strength of the Au—Pt alloy wire material is preferably as high as possible, the upper limit is preferably 1500 MPa.

There is no particular limitation to the shape of the embolization coil according to the present invention described hereinbefore. The embolization coil has a coil shape obtained by subjecting a straight wire material to winding processing at least once. This, however, is not intended as limiting the number of times of the winding processing. Also, there is no limitation to the number of windings of the coil, the diameter of the coil, and the length of the coil. A currently known embolization coil has a secondary coil shape produced by two times of winding processing (primary coil processing and secondary coil processing). The embolization coil according to the present invention may have this secondary coil shape.

Also, there is no limitation to the wire diameter of the wire material made of the Au—Pt alloy insofar as the wire material serves the purpose of an embolization coil, which is transferred inside a human body (through blood vessels). Generally, a preferable wire diameter is 10 μm or more and 100 μm or less.

Next, a method according to the present invention for producing an embolization coil will be described. The embolization coil according to the present invention can be produced by subjecting an Au—Pt alloy wire material having the above-described configuration to winding processing so as to impart a coil shape to the Au—Pt alloy wire material. The winding processing step is performed at least once. An embolization coil having a secondary coil shape is produced by producing a spiral wire material (primary coil) having an ultra-small diameter and then subjecting the primary coil to additional winding processing so as to impart a secondary coil shape to the coil.

In the present invention, the treatment to impart morphological stability to the embolization coil formed by the winding processing (morphological stability treatment) is performed by heating, within a predetermined temperature range, the wire material that is being processed with the wire material secured in a wound state. By the heating, the wire material is reformed to the shape specified by the processing that the wire material is undergoing. The coil that has undergone the morphological stability treatment maintains the shape specified by the winding processing after the load of the processing is released. Further, the coil exhibits shape restorability against the deformation that the coil undergoes afterward.

In this respect, the heating temperature of the morphological stability treatment is specified at 350° C. or higher and 550° C. or lower. This is for the purpose of ensuring the essential characteristics required of an artifact-free embolization coil while realizing morphological stability effects. Specifically, if the heating temperature is so much low as less than 350° C., the morphological stability effects cannot be obtained, and thus the coil that has undergone the winding processing is morphologically instable. If the heating temperature is too high, the material structure may drastically change, causing the magnetic susceptibility of the wire material to fluctuate greatly.

According to the inventors, if an Au—Pt alloy wire material is heated at 350° C. or higher, the crystal particle diameter in the material structure of the wire material starts to change. It is also at this temperature or higher that a concern over generation of a separate phase emerges. If an Au—Pt alloy wire material is heated at 550° C. or higher, the crystal particle diameter (average value of average crystal particle diameters) becomes excessively large. Also, generation of a separate phase causes a wider variation in measured values of the crystal particle diameter. The magnetic susceptibility of the wire material at this time has changed from its pre-processing magnetic susceptibility. In light of this, the upper limit of the heating temperature of the morphological stability treatment is specified at 500° C. or lower. A more preferable range of the heating temperature is 400° C. or higher and 500° C. or lower.

The morphological stability treatment is performed as part of winding processing. In winding processing, a wire material (which may be a wire material processed into a spiral shape in primary processing) is repeatedly wound around and fixed to a suitable jig, such as a bar-shaped jig and a cylindrical jig, and thus the wire material is imparted a coil shape. In this winding processing, the morphological stability treatment can be performed by heating the wire material wound around and fixed to the jig.

The morphological stability treatment needs to be performed at least once in the winding processing performed at least once. In production of an embolization coil having a secondary coil shape, the first winding processing, which is for obtaining a primary coil, is performed at a processing rate high enough to make morphological stability treatment unnecessary. It is in the winding processing to obtain a secondary coil shape that morphological stability treatment is preferably performed.

The wire material made of the Au—Pt alloy processed into the embolization coil according to the present invention is obtained by processing an Au—Pt alloy ingot or an alloy material into a fine wire. The alloy material is obtained by roughly processing an ingot. When this material is processed into the wire material for the embolization coil, the processing rate is typically set at 50% or more and 100% or less. In this respect, the material is processed within such a temperature range that the magnetic susceptibility of the Au—Pt alloy does not fluctuate, as described above. The processing temperature is specified at 300° C. or lower. The manner of processing may be any one or combination of processings known in the art, such as drawing processing and rolling processing. The Au—Pt alloy material has a processability optimum enough to be processed into a wire material without cracking and/or rupture.

The method for producing the Au—Pt alloy includes basic steps of: preparing a supersaturated solid solution alloy of α phase from an alloy whose composition has been adjusted at a Pt concentration of 24 mass % or more and less than 34 mass %, with the balance being Au; and subjecting the supersaturated solid solution alloy to heat treatment at 600 to 1000° C., thereby causing a Pt-rich phase to be deposited. In this manner, the Au—Pt alloy is produced.

In production of the Au—Pt alloy, a supersaturated solid solution of single α phase is prepared first, and then a Pt-rich phase is deposited. This is for the purpose of adjusting the magnetic susceptibility by controlling the amount of deposition of the Pt-rich phase within a proper range. An example of the method of forming the supersaturated solid solution of single α phase of the Au—Pt alloy is typical solutionizing treatment. This solutionizing treatment includes, after an alloy ingot is produced by melting and casting or some other method, heating the alloy ingot to an α phase region and rapidly cooling the alloy ingot.

A preferable method of obtaining a supersaturated solid solution alloy of single α phase is to perform single-phase treatment of an alloy ingot a plurality of times. Single-phase treatment refers to one set of a cold working step and a heat treatment step. The cold working step is to subject an alloy ingot obtained by melting and casting to cold working (such as cold rolling, cold forging, cold wire-drawing, and cold extrusion). The heat treatment step is to subject the alloy ingot to heat treatment at a temperature (preferably 1150 to 1250° C.) higher than a temperature set for the α phase region based on the alloy composition. The cold working in the single-phase treatment is for the purpose of breaking a cast structure obtained by melting and casting, thereby facilitating movement of atoms in the heat treatment that follows. The heat treatment is for the purpose of overcoming a casting-caused segregation and also causing α phase alone to constitute the phase configuration of the alloy. Specifically, the heat treatment causes a deposit in the alloy to return to α phase, and finally eliminates the deposit. The single-phase treatment, which is made up of cold working and heat treatment, is repeated to be performed a plurality of times (preferably performed twice or more). This causes a segregation to be overcome and a deposit to be eliminated, resulting in a uniformized material composition and a single-phase configuration.

The supersaturated solid solution alloy of single α phase thus obtained is subjected to heat treatment so that a Pt-rich phase is deposited in the α phase. In this manner, the Au—Pt alloy applied to the present invention is produced. The heat treatment for deposition of the Pt-rich phase is performed at a temperature within the "α1+α2" region of the phase diagram, below the α phase region. A specific temperature range is specified at 600 to 1000° C.

Effects of the Invention

As has been described hereinbefore, the embolization coil according to the present invention has an optimum morphological stability. Also, the embolization coil is made of a predetermined Au—Pt alloy and has suitable magnetic susceptibility. The embolization coil according to the present invention can be used in a magnetic field environment such as in an MRI without an artifact. Further, the constituent elements of the embolization coil ensure characteristics required of medical instruments, such as biocompatibility and anti-corrosion property.

BRIEF DESCRIPTION OF THE DRAWINGS

FIG. 2 illustrates transverse cross-sectional structures of alloy wire materials that have undergone morphological stability treatment.

MODES FOR CARRYING OUT THE INVENTION

Figure 1:
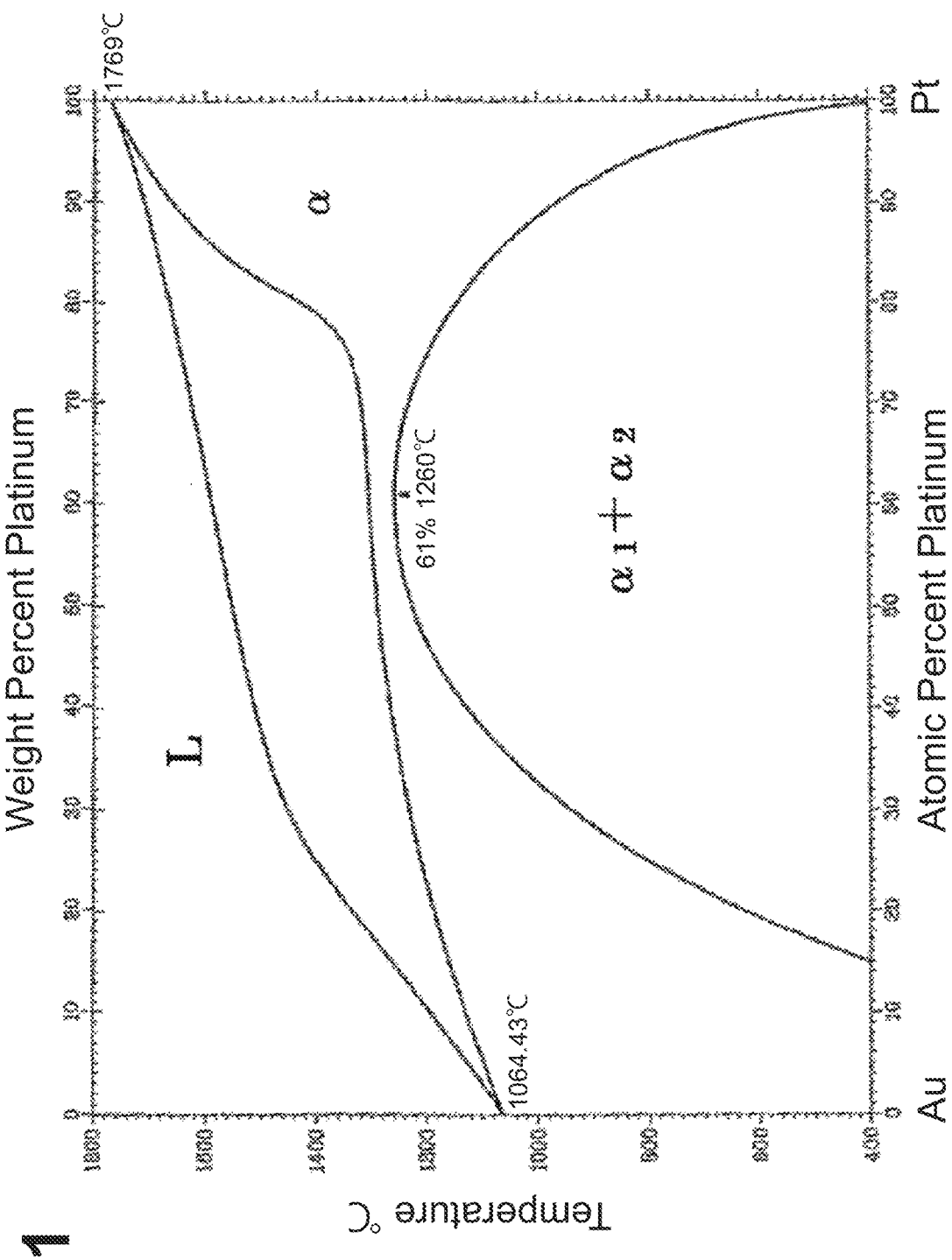
FIG. 1 is a phase diagram of an Au—Pt system alloy.

An embodiment of the present invention will be described. In this embodiment, an Au—Pt alloy ingot having a proper magnetic susceptibility was produced, and this Au—Pt alloy ingot was used as a material processed into a wire material. Then, the wire material was processed into a secondary coil shape. In this manner, an embolization coil was produced. In this coil processing step, which involved two times of winding processing, morphological stability treatment was performed during the secondary coil processing. In this embodiment, the morphological stability treatment was performed under a plurality of different conditions to produce different embolization coils. Then, the embolization coils were evaluated as to properties such as coil morphological stability and bulk susceptibility. Also, the embolization coils were examined as to how the constituent material structures of the embolization coils differed from each other.

Production of Au—Pt Alloy Material

In this embodiment, an Au—Pt alloy having a Pt concentration of 30 mass % was produced. Pure Au and pure Pt (99.99% pure products of TANAKA KIKINZOKU KOGYO K.K.) were weighed to an intended composition, and the resulting alloy was subjected to high-frequency melting and casted into an alloy ingot. The alloy ingot was produced at a standard weight of 60 g. The alloy ingot obtained by melting and casting was subjected to hot forging at a forging temperature of 1000° C.

Next, the alloy ingot was subjected to single-phase treatment, and thus a supersaturated solid solution alloy of single α phase was produced. First in the single-phase treatment, the alloy ingot was subjected to cold working, namely, cold groove rolling (at a processing rate of 40%). Then, the alloy ingot was heated at 1200° C. for one hour or longer. Then, the alloy ingot was put into water, where the alloy ingot was rapidly cooled. This single-phase treatment, which was a combination of cold working and heat treatment, was performed three times.

Then, the alloy that has undergone the single-phase treatment was subjected to drawing processing. After the drawing processing, the alloy was subjected to heat treatment so that a Pt-rich phase was deposited. The heat treatment temperature was set at 800° C. In the heat treatment, the alloy was heated and, after a period of time, put into iced water, where the alloy was rapidly cooled. As a result of this heat treatment, an Au—Pt alloy material (wire diameter: 2 mm) was obtained.

Production of Au—Pt Alloy Wire Material

The Au—Pt alloy material produced in the above-described manner was processed into an Au—Pt alloy wire material that was to be processed into an embolization coil. In the processing to obtain the wire material, the Au—Pt alloy material was subjected to cold drawing processing using a plurality of dies. In this manner, a wire material (wire diameter: 38 μm) made of the Au—Pt alloy was produced. The processing rate was 99.97%.

Production of Embolization Coil

Next, the Au—Pt alloy wire material produced in the above-described manner was subjected to winding processing twice, and thus an embolization coil having a secondary coil shape was produced. First, primary processing was performed. In the primary processing, the Au—Pt alloy wire material (wire diameter: 38 μm) was wound around a fine core wire (outer diameter of 1 mm, made of SUS304). As a result, the Au—Pt alloy wire material was processed into a spiral wire material (primary coil) having an outer diameter of 0.25 mm and an inner diameter of 0.18 mm. This spiral wire material was wound around and fixed to a core bar (outer diameter of 1.2 mm, made of SUS304). In this secondary coil processing, the spiral wire material was processed into a secondary coil shape with reference values (target values) of the outer diameter and the inner diameter set at 2.0 mm and 1.5 mm, respectively.

During the secondary coil processing, morphological stability treatment was performed. In the morphological stability treatment, the wire material (primary coil) wound around and fixed to the core bar was placed on a heat treatment boat and inserted into a horizontal tube furnace, where the wire material was subjected to heat treatment. The morphological stability treatment was attempted at a plurality of heat treatment temperatures in the range of 100° C. to 800° C. for a common heat treatment period of time of 30 minutes.

In the coil processing of the Au—Pt alloy wire material, a sample obtained at each of the temperatures of the morphological stability treatment was subjected to various kinds of measurement and evaluation, namely, structure observation, measurement of average crystal particle diameter, and evaluation of magnetic susceptibility and morphological stability.

Structure Observation and Measurement of Average Crystal Particle Diameter

A transverse cross-section of the Au—Pt alloy wire material that has undergone the secondary coil processing was subjected to SIM (scanning ion microscope) image observation. In the SIM image observation, the Au—Pt alloy wire material was precisely cut by FIB processing (focused ion beam processing, equipment name: FB-2000A) to form an observation surface. The structure of the obtained cross-section was observed through an SIM image, and the average crystal particle diameter of the cross-section was measured based on the SIM image. In this embodiment, the average crystal particle diameter was measured based on an SIM image represented by a field of vision of 8-by-8 μm at a magnification of approximately 16000 times.

How the average crystal particle diameter is measured by the linear intercept method will be described by referring to cross-sectional structures of Au—Pt alloy wire materials obtained by coil processing with morphological stability treatment performed during the coil processing at 300° C., 500° C., and 700° C. FIG. 2 illustrates transverse cross-sectional structures of alloy wire materials treated at the above-described temperatures. The average crystal particle diameter is measured by the linear intercept method according to the following work procedure.

(i) On a structure photograph, draw lines along grain boundaries using a pen or another writing instrument so as to make the grain boundaries more recognizable.
(ii) Draw a plurality of lines on arbitrary portions of the photograph.
(iii) Count the number ($n_c$) of points (intersections) at which the lines in (ii) and the grain boundaries meet.
(iv) Compare the length of each of the lines in (ii) against a scale in an observation region and correct the length to an actual length (L).
(v) Calculate an average crystal particle diameter ($R_A$) by solving the following formula.

$$R_A = L/n_g \quad \text{[Mathematical formula 1]}$$

In the above-described measurement of the average crystal particle diameter by the linear intercept method, a plurality of lines are drawn in (ii), and the average crystal particle diameter is calculated on each of the lines. In this embodiment, 30 lines were drawn, and average crystal particle diameters were calculated on the 30 lines. Then, the resulting 30 pieces of data were used to calculate an average value ($X_{RA}$) and a standard deviation ($\sigma_{RA}$). The standard deviation ($\sigma_{RA}$) is calculated by solving the following formula.

$$X_{RA} = (R_{A1} + R_{A2} + \ldots R_{An})/n$$

$$\sigma_{RA}^2 = [(R_{A1} - X_{RA})^2 + (R_{A2} - X_{RA})^2 + \ldots (R_{An} - X_{RA})^2]/n \quad \text{[Mathematical formula 2]}$$

[$R_{An}$=n-th $R_A$ (in this embodiment, n=1 to 30), n=number of pieces of data (in this embodiment, n=30)]

In this embodiment, average crystal particle diameters of wire materials subjected to morphological stability treatment at 300° C., 500° C., and 700° C. were measured. Tables 1 to 3 list exemplary results of average crystal particle diameters measured. Also in this embodiment, average crystal particle diameters of wire materials subjected to morphological stability treatment at 350° C. and 550° C. were measured, and average crystal particle diameters of wire materials in pre-coil processing state (that is, wire materials without morphological stability treatment) were measured.

TABLE 1

| Heat treatment temperature (° C.) | n | $R_A$ Average crystal particle diameter (μm) | $R_A$ Maximum value (μm) | $R_A$ Minimum value (μm) | $X_{RA}$ Average value of $R_A$ (μm) | $\sigma_{RA}$ Standard deviation |
|---|---|---|---|---|---|---|
| 300 | 1 | 0.19 | 0.25 | 0.15 | 0.19 | 0.023 |
| | 2 | 0.20 | | | | |
| | 3 | 0.22 | | | | |
| | 4 | 0.18 | | | | |
| | 5 | 0.19 | | | | |
| | 6 | 0.16 | | | | |
| | 7 | 0.21 | | | | |
| | 8 | 0.18 | | | | |
| | 9 | 0.20 | | | | |
| | 10 | 0.21 | | | | |
| | 11 | 0.16 | | | | |
| | 12 | 0.15 | | | | |
| | 13 | 0.20 | | | | |
| | 14 | 0.22 | | | | |
| | 15 | 0.23 | | | | |
| | 16 | 0.25 | | | | |
| | 17 | 0.22 | | | | |
| | 18 | 0.20 | | | | |
| | 19 | 0.21 | | | | |
| | 20 | 0.22 | | | | |
| | 21 | 0.18 | | | | |
| | 22 | 0.19 | | | | |
| | 23 | 0.16 | | | | |
| | 24 | 0.16 | | | | |
| | 25 | 0.17 | | | | |
| | 26 | 0.19 | | | | |
| | 27 | 0.20 | | | | |
| | 28 | 0.21 | | | | |
| | 29 | 0.18 | | | | |
| | 30 | 0.21 | | | | |

TABLE 2

| Heat treatment temperature (° C.) | n | $R_A$ Average crystal particle diameter (μm) | $R_A$ Maximum value (μm) | $R_A$ Minimum value (μm) | $X_{RA}$ Average value of $R_A$ (μm) | $\sigma_{RA}$ Standard deviation |
|---|---|---|---|---|---|---|
| 500 | 1 | 0.30 | 0.62 | 0.21 | 0.30 | 0.081 |
| | 2 | 0.25 | | | | |
| | 3 | 0.27 | | | | |
| | 4 | 0.25 | | | | |
| | 5 | 0.22 | | | | |
| | 6 | 0.25 | | | | |
| | 7 | 0.23 | | | | |
| | 8 | 0.23 | | | | |
| | 9 | 0.23 | | | | |
| | 10 | 0.34 | | | | |
| | 11 | 0.26 | | | | |
| | 12 | 0.30 | | | | |
| | 13 | 0.27 | | | | |
| | 14 | 0.42 | | | | |
| | 15 | 0.33 | | | | |
| | 16 | 0.42 | | | | |
| | 17 | 0.62 | | | | |
| | 18 | 0.27 | | | | |
| | 19 | 0.36 | | | | |
| | 20 | 0.32 | | | | |
| | 21 | 0.23 | | | | |
| | 22 | 0.33 | | | | |
| | 23 | 0.25 | | | | |
| | 24 | 0.33 | | | | |
| | 25 | 0.21 | | | | |
| | 26 | 0.26 | | | | |
| | 27 | 0.34 | | | | |

TABLE 2-continued

| Heat treatment temperature (° C.) | n | $R_A$ Average crystal particle diameter (μm) | $R_A$ Maximum value (μm) | $R_A$ Minimum value (μm) | $X_{RA}$ Average value of $R_A$ (μm) | $\sigma_{RA}$ Standard deviation |
|---|---|---|---|---|---|---|
| | 28 | 0.25 | | | | |
| | 29 | 0.30 | | | | |
| | 30 | 0.25 | | | | |

TABLE 3

| Heat treatment temperature (° C.) | n | $R_A$ Average crystal particle diameter (μm) | $R_A$ Maximum value (μm) | $R_A$ Minimum value (μm) | $X_{RA}$ Average value of $R_A$ (μm) | $\sigma_{RA}$ Standard deviation |
|---|---|---|---|---|---|---|
| 700 | 1 | 0.35 | 0.62 | 0.22 | 0.38 | 0.090 |
| | 2 | 0.36 | | | | |
| | 3 | 0.29 | | | | |
| | 4 | 0.33 | | | | |
| | 5 | 0.29 | | | | |
| | 6 | 0.22 | | | | |
| | 7 | 0.29 | | | | |
| | 8 | 0.38 | | | | |
| | 9 | 0.27 | | | | |
| | 10 | 0.43 | | | | |
| | 11 | 0.32 | | | | |
| | 12 | 0.46 | | | | |
| | 13 | 0.35 | | | | |
| | 14 | 0.38 | | | | |
| | 15 | 0.50 | | | | |
| | 16 | 0.44 | | | | |
| | 17 | 0.53 | | | | |
| | 18 | 0.42 | | | | |
| | 19 | 0.50 | | | | |
| | 20 | 0.62 | | | | |
| | 21 | 0.37 | | | | |
| | 22 | 0.52 | | | | |
| | 23 | 0.33 | | | | |
| | 24 | 0.36 | | | | |
| | 25 | 0.32 | | | | |
| | 26 | 0.29 | | | | |
| | 27 | 0.39 | | | | |
| | 28 | 0.34 | | | | |
| | 29 | 0.43 | | | | |
| | 30 | 0.29 | | | | |

Measurement of Bulk Susceptibility

Each of the Au—Pt alloy wire materials was subjected to measurement of bulk susceptibility. The magnetic susceptibility was measured using a sensitive and portable magnetic balance, MSB-AUTO (product of Sherwood Scientific Ltd.) (measurement temperature: 27° C.). The wire materials subjected to measurement of bulk susceptibility were those subjected to morphological stability treatment at the above-described temperatures and those in pre-coil processing state (that is, wire materials without morphological stability treatment).

Evaluation of Morphological Stability

The morphological stability was evaluated by measuring the inner-diameter return ratio of each of the embolization coils that have undergone the secondary coil processing together with the morphological stability treatment. Each embolization coil that has undergone the secondary coil processing was removed off the core bar, and the inner diameter of the secondary coil produced was measured using a digital scope (VHX-900, product of KEYENCE CORPORATION). Based on this measured value and the following formula, an inner-diameter return ratio ($K_D$) was calculated at the time when the secondary coil was unloaded, that is, removed off the core bar.

$$K_D(\%)=((D_2-D_1)/D_1)\times100 \quad \text{[Mathematical formula 3]}$$

($D_1$: core bar diameter (1.2 mm), $D_2$: inner diameter of unloaded secondary coil)

In addition to measurement of the inner-diameter return ratio, a tensile test was performed to measure the tensile strength of the wire material. Measurement of the tensile strength is for the purpose of evaluating the morphological stability that the wire material would have when used as an embolization coil. If the tensile strength of the wire material changes (degrades) due to heat treatment, it is possible for the wire material to be easily deformed when used as an embolization coil. In light of this, the tensile strength is measured to examine this possibility. The tensile test was performed using Strong life Ell-L05 (product of Toyo Seiki Seisaku-sho, Ltd.) with a load cell of 50N and at a test speed of 10 mm/minute.

Description will be made with regard to results of measurement and evaluation of the various items described above. First, results associated with the average crystal particle diameter are listed on Table 4.

TABLE 4

| Heat treatment temperature (° C.) | $X_{RA}$ Average value of $R_A$ (μm) | $\sigma_{RA}$ Standard deviation |
|---|---|---|
| No heat treatment | 0.19 | 0.023 |
| 300° C. | 0.19 | 0.023 |
| 350° C. | 0.22 | 0.029 |
| 500° C. | 0.30 | 0.081 |
| 550° C. | 0.34 | 0.084 |
| 700° C. | 0.38 | 0.090 |

Referring to the average value ($X_{RA}$) of average crystal particle diameters on Table 4, the average value ($X_{RA}$) starts changing at the coil wire material subjected to the morphological stability treatment performed at 350° C. The same applies in the standard deviation ($\sigma_{RA}$). $X_{RA}$ and $\sigma_{RA}$ tend to increase as the temperature of the morphological stability treatment increases.

Figure 3:
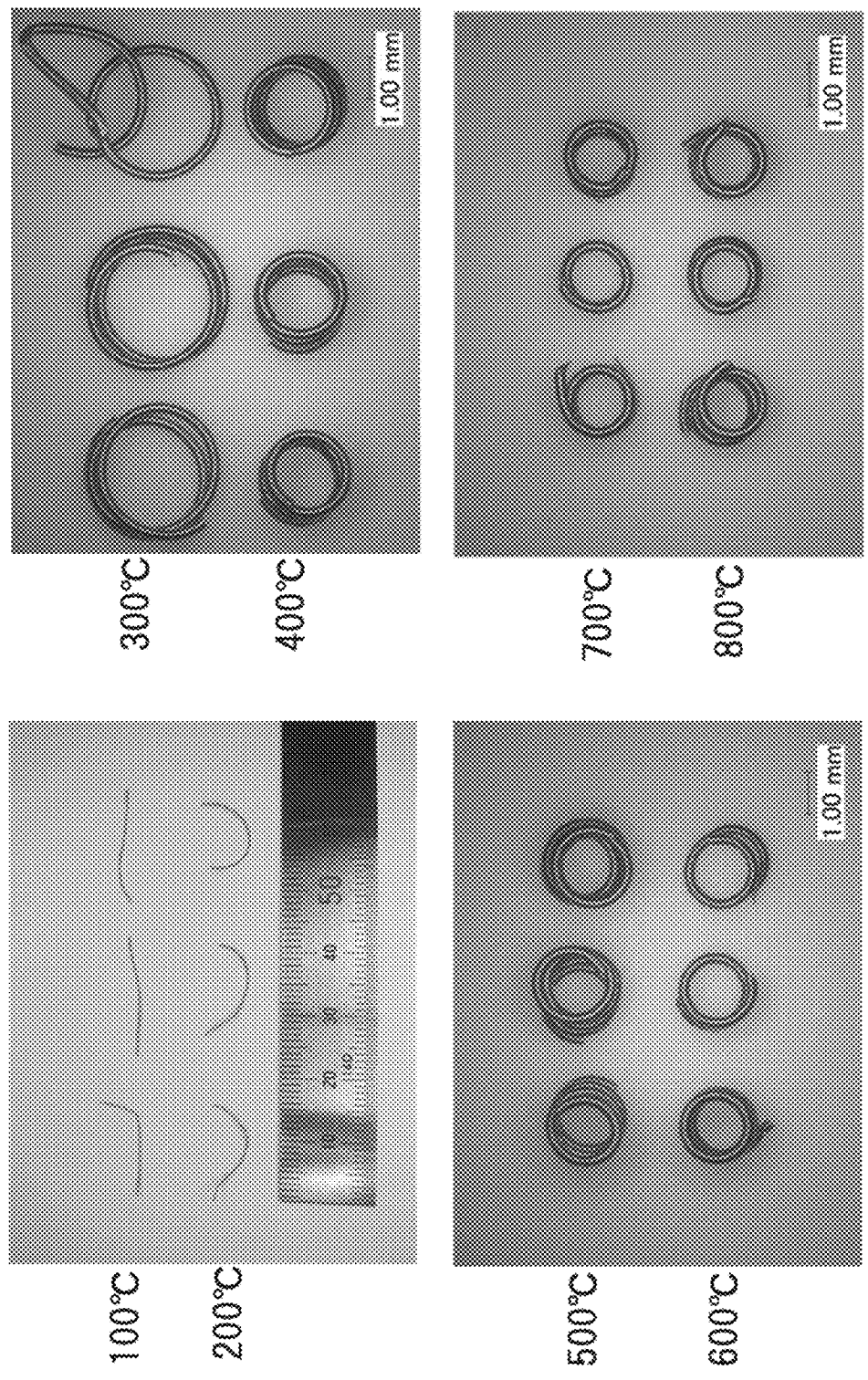
FIG. 3 shows photographs of external appearances of secondary coils produced with morphological stability treatment performed at different treatment temperatures.

Now, how the temperature of the morphological stability treatment is related to magnetic susceptibility and morphological stability will be examined. FIG. 3 illustrates photographs of external appearances of secondary coils (embolization coils) produced with morphological stability treatment performed at different treatment temperatures (100° C. to 800° C.). As seen from the photographs, the secondary coil processing is not complete at temperatures 100° C. and 200° C. in that the unloaded coils are shaped like primary coils, which are not subjected to the secondary coil processing yet. Also, the coils treated at 300° C. increased in inner diameter after unloading.

Figure 4:
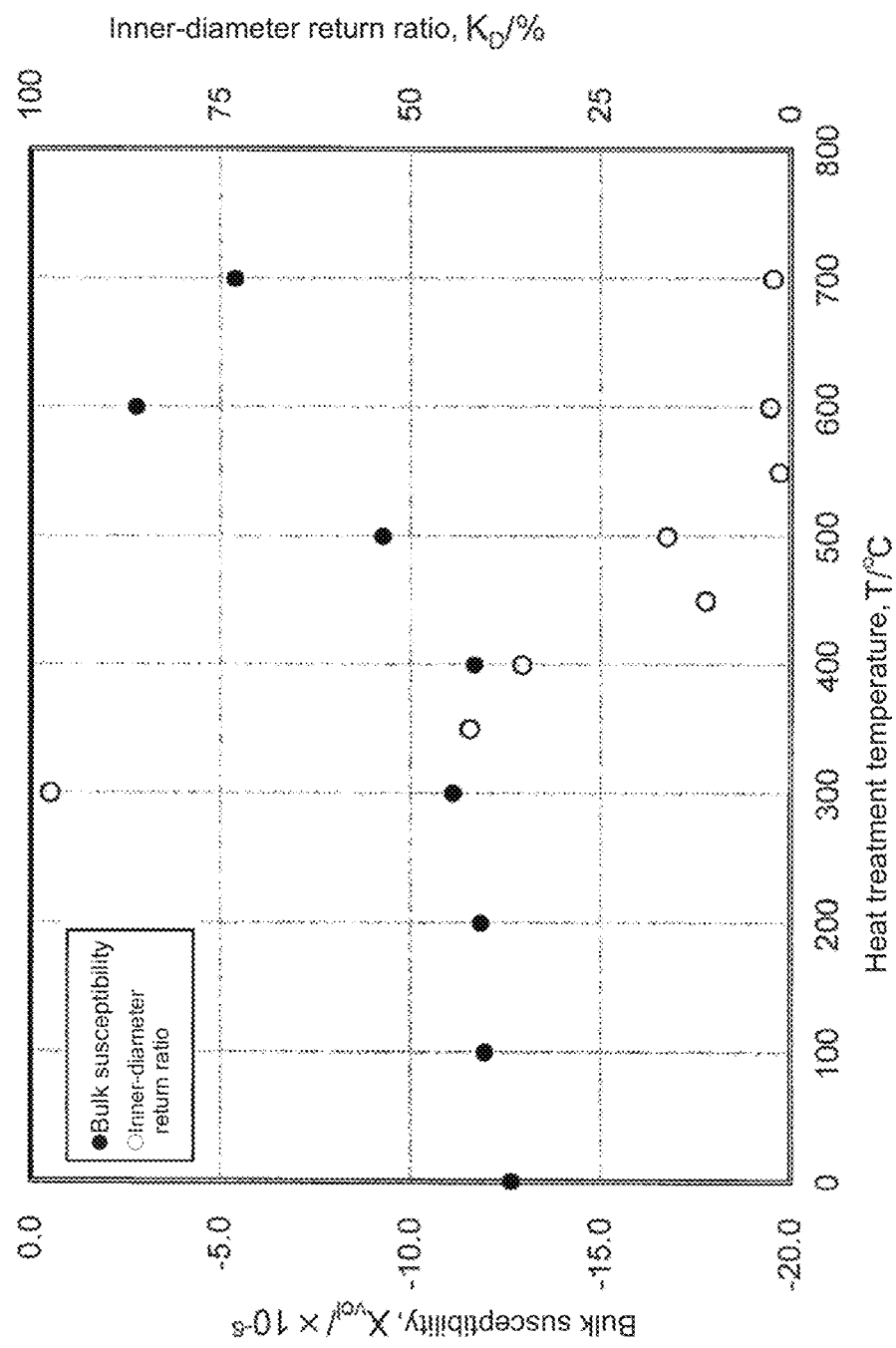
FIG. 4 illustrates results of measurement of inner-diameter return ratios and bulk susceptibilities of the secondary coils produced at different treatment temperatures.

FIG. 4 illustrates results of measurement of inner-diameter return ratios and bulk susceptibilities of the secondary coils produced at different treatment temperatures. In the heat treatments at 300° C. or lower, the inner-diameter return ratio is 100% or more, indicating that morphological stability is not obtained as early as immediately after the secondary coil processing. It is in the treatments at 350° C. or higher that the inner-diameter return ratio falls below 50%.

Figure 5:
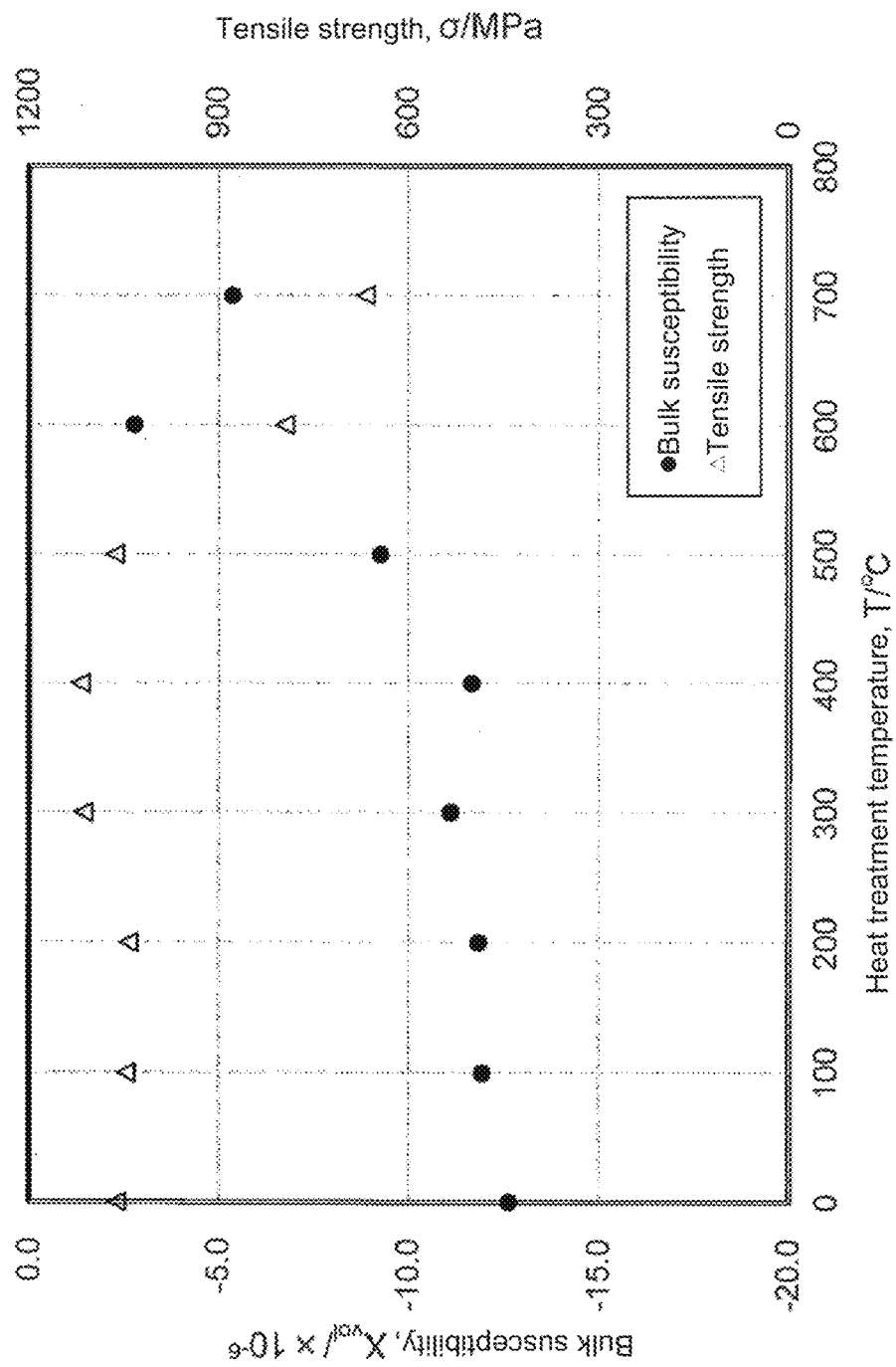
FIG. 5 illustrates results of measurement of tensile strengths and bulk susceptibilities of the secondary coils produced at different treatment temperatures.

FIG. 5 illustrates results of measurement of tensile strengths and bulk susceptibilities of the secondary coils produced at different treatment temperatures. This graph shows a sharp decrease in tensile strength at high heat treatment temperatures (600° C. and higher).

Now, both FIGS. 4 and 5 will be examined. The heat treatment temperature of the morphological stability treatment influences all of the inner-diameter return ratio, tensile strength, bulk susceptibility. First, this tendency will be examined from an artifact-free standpoint. In the heat treatment performed at 600° C., which is in excess of 500° C., the bulk susceptibility is more positive than −5 ppm, which is a great shift toward the positive side from the pre-processing bulk susceptibility (−12.5 ppm). This leads to the assumption that for an embolization coil to have an artifact-free configuration (bulk susceptibility: −13 ppm or more and −5 ppm or less), the heat treatment needs to be performed at 500° C. or lower.

Then, the above tendency will be examined from the standpoint of morphological stability required of an embolization coil. First, the least requirement that a secondary coil shape be maintained immediately after the secondary processing will be evaluated using return ratio. In the heat treatment performed at 300° C. or lower, the return ratio is too large. Some samples do not have a secondary coil shape in the first place, such as the samples subjected to heat treatment at 100° C. and 200° C. This leads to the requirement that in terms of shape immediately after processing (immediately after production), the heat treatment needs to be performed at a temperature of 350° C. or higher.

It is noted, however, that no matter how stable the obtained secondary coil shape is, the secondary coil cannot exhibit morphological stability in actual applications without a suitable level of strength. In light of the circumstances, the tensile strength results lead to the assumption that at 600° C. or higher, the tensile strength degrades too greatly to implement an optimum embolization coil.

Thus, with both return ratio and tensile strength taken into consideration, the temperature of the morphological stability treatment should be set within the temperature range of 350° C. or higher and 550° C. or lower. Coils produced within this temperature range exhibit an optimum range of bulk susceptibility (bulk susceptibility: −13 ppm or more and −5 ppm or less).

Thus, with a balance between magnetic susceptibility and morphological stability taken into consideration, the temperature of the morphological stability treatment should be set within the temperature range of 350° C. or higher and 550° C. or lower. In this respect, the material structure of an Au—Pt alloy wire material treated within this temperature range will be examined. The results listed on Table 4 show an increase in average crystal particle diameter in the treatment performed at 350° C. or higher. It is also at this temperature or higher that a separate phase is presumed to be generated, judging from how the standard deviation of the average crystal particle diameter changes. Although the increase in crystal particle diameter and generation of a separate phase should basically be avoided, these phenomena are tolerable to some degree. This is because if the treatment temperature is 350° C. or higher but not excessively higher, the magnetic susceptibility is maintained within a proper range. Then, the material structure of the Au—Pt alloy wire material according to the present invention can be specified as follows, with changes in magnetic susceptibility taken into consideration: the average value of average crystal particle diameters is set at 0.20 μm or more and 0.35 μm or less.

INDUSTRIAL APPLICABILITY

The embolization coil made of the Au—Pt alloy according to the present invention has a magnetic susceptibility optimum for preventing artifacts. The embolization coil also has a morphological stability optimum enough to take optimum forms while the embolization coil is being inserted and/or handled in an affected part of body when the embolization coil is in use. Also, the embolization coil serves as a medical instrument optimum in biocompatibility and anti-corrosion property.

The invention claimed is:

1. An embolization coil comprising a wire material made of an Au—Pt alloy,
   wherein the wire material constituting the embolization coil has such a composition that a Pt concentration is 24 mass % or more and less than 34 mass %, with the balance being Au, and the wire material has such a material structure that a Pt-rich phase of an Au—Pt alloy having a Pt concentration of 1.2 to 3.8 times a Pt concentration of an α phase is distributed in an α phase matrix,
   wherein the wire material has a bulk susceptibility of −13 ppm or more and −5 ppm or less,
   wherein the wire material has a tensile strength of 800 MPa or more,
   wherein in a material structure of a transverse cross-section of the wire material there are a plurality of crystal particles with diameters where the average diameter of the crystal particles measured by a linear intercept method is 0.20 μm or more and 0.35 μm or less, and the standard deviation of the crystal particles' diameters is 0.025 μm or more and 0.085 μm or less,
   wherein the embolization coil has a spiral primary coil shape and a secondary coil shape, and
   wherein the embolization coil's secondary coil shape has an inner diameter $D_1$ when the embolization coil is loaded to a 1.2 mm diameter core bar and an inner diameter $D_2$ when unloaded from the core bar, the embolization coil has an inner-diameter return rate ($K_D$) of 50% or less, which is represented by the following formula:

$$K_D (\%) = ((D_2 - D_1)/D_1) \times 100.$$

2. The embolization coil according to claim 1, wherein the wire material made of the Au—Pt alloy has a wire diameter of 10 μm or more and 100 μm or less.

3. A method for producing an embolization coil according to claim 1, wherein the embolization coil has a secondary coil shape, the method comprising
   performing a winding processing step at least once, the winding processing step comprising subjecting a wire material made of an Au—Pt alloy to winding processing, the wire material having such a composition that a Pt concentration is 24 mass % or more and less than 34 mass %, with the balance being Au, the wire material comprising a Pt-rich phase of an Au—Pt alloy distributed in an α phase matrix, the Au—Pt alloy of the Pt-rich phase having a Pt concentration of 1.2 to 3.8 times a Pt concentration of an α phase, the wire material having a bulk susceptibility −13 ppm or more and −5 ppm or less,
   wherein the morphological stability treatment is performed when the winding processing step comprises forming the secondary coil shape, and
   wherein the winding processing step comprises performing morphological stability treatment at least once, the morphological stability treatment comprising, with the wire material secured in a wound state, heating and holding the wire material at a temperature of 350° C. or higher and 550° C. or lower.

4. The method for producing the embolization coil according to claim 3, comprising processing a material of the Au—Pt alloy at a processing rate of 50% or more so as to produce the wire material to be processed into the embolization coil.

5. A method for producing an embolization coil according to claim 2, the method comprising performing a winding processing step at least once, the winding processing step comprising subjecting a wire material made of an Au—Pt alloy to winding processing, the wire material having such a composition that a Pt concentration is 24 mass % or more and less than 34 mass %, with the balance being Au, the wire material comprising a Pt-rich phase of an Au—Pt alloy distributed in an α phase matrix, the Au—Pt alloy of the Pt-rich phase having a Pt concentration of 1.2 to 3.8 times a Pt concentration of an α phase, the wire material having a bulk susceptibility −13 ppm or more and −5 ppm or less, wherein the winding processing step comprises performing morphological stability treatment at least once, the morphological stability treatment comprising, with the wire material secured in a wound state, heating and holding the wire material at a temperature of 350° C. or higher and 550° C. or lower.

* * * * *